(12) United States Patent
Matityahu

(10) Patent No.: US 7,951,179 B2
(45) Date of Patent: May 31, 2011

(54) BONE ATTACHMENT SCREW

(75) Inventor: Amir M. Matityahu, Los Altos, CA (US)

(73) Assignee: Anthem Orthopaedics LLC, Los Altos, CA (US)

( * ) Notice: Subject to any disclaimer, the term of this patent is extended or adjusted under 35 U.S.C. 154(b) by 885 days.

(21) Appl. No.: 11/588,037

(22) Filed: Oct. 25, 2006

(65) Prior Publication Data
US 2007/0162016 A1    Jul. 12, 2007

Related U.S. Application Data

(60) Provisional application No. 60/730,491, filed on Oct. 25, 2005.

(51) Int. Cl.
*A61F 2/30* (2006.01)

(52) U.S. Cl. .................................................. 606/300

(58) Field of Classification Search .............. 606/61, 606/69, 70, 71, 73, 266, 280–299, 300–321; 411/411, 417, 418, 421
See application file for complete search history.

(56) References Cited

U.S. PATENT DOCUMENTS

| | | | |
|---|---|---|---|
| 2,267,925 A | 2/1941 | Johnston | |
| 2,699,774 A | 1/1955 | Livingston | |
| 3,255,747 A | 9/1966 | Cochran, et al. | |
| 3,463,148 A | 8/1969 | Treace | |
| 4,219,015 A | 8/1980 | Steinemann | |
| 4,297,993 A | 11/1981 | Harle | |
| 4,484,570 A | 11/1984 | Sutter et al. | |
| 5,057,111 A | 10/1991 | Park | |
| 5,108,399 A | 4/1992 | Eitenmuller et al. | |
| 5,190,544 A * | 3/1993 | Chapman et al. | 606/71 |
| 5,329,959 A * | 7/1994 | Owen et al. | 137/315.17 |
| 5,470,333 A | 11/1995 | Ray | |
| 5,545,164 A | 8/1996 | Howland | |
| 5,603,713 A | 2/1997 | Aust et al. | |
| 5,616,144 A | 4/1997 | Yapp et al. | |
| 5,735,853 A | 4/1998 | Olerud | |
| 5,954,722 A * | 9/1999 | Bono | 606/281 |
| 6,214,012 B1 | 4/2001 | Karpman et al. | |
| 6,235,033 B1 * | 5/2001 | Brace et al. | 606/288 |
| 6,293,949 B1 | 9/2001 | Justis et al. | |
| 6,331,179 B1 | 12/2001 | Freid et al. | |
| 6,342,055 B1 | 1/2002 | Eisermann et al. | |
| 6,544,266 B1 | 4/2003 | Roger et al. | |
| 6,575,975 B2 | 6/2003 | Brace et al. | |
| 6,663,632 B1 * | 12/2003 | Frigg | 606/246 |
| 6,783,382 B2 | 8/2004 | Felps | |

(Continued)

FOREIGN PATENT DOCUMENTS
WO    WO 2004/084701 A2    10/2004

*Primary Examiner* — Eduardo C Robert
*Assistant Examiner* — Christopher Beccia
(74) *Attorney, Agent, or Firm* — Dorsey & Whitney LLP

(57) ABSTRACT

A bone fastening assembly for use with a screw and including a bone plate and a bushing having a bore adapted for receiving the screw. The bone plate has a substantially planar portion and is provided with a hole in the portion for receiving the bushing. The portion of the bone plate and the bushing are cooperatively configured for providing pivotal movement of the bushing within the hole about a pivot axis and restricting the pivot axis to a plane extending in the portion of the bone plate. A new bone attachment screw for use with the bone fastening assembly is provided.

7 Claims, 12 Drawing Sheets

U.S. PATENT DOCUMENTS

| | | |
|---|---|---|
| 6,786,909 B1 | 9/2004 | Dransfeld et al. |
| 6,890,334 B2 | 5/2005 | Brace et al. |
| 6,893,443 B2 | 5/2005 | Frigg et al. |
| 6,908,466 B1 | 6/2005 | Bonutti et al. |
| 6,916,321 B2 * | 7/2005 | TenHuisen et al. ........... 606/312 |
| 6,916,483 B2 | 7/2005 | Ralph et al. |
| 7,195,633 B2 | 3/2007 | Medoff et al. |
| 7,547,305 B2 | 6/2009 | Rapp |
| 2002/0058939 A1 * | 5/2002 | Wagner et al. .................. 606/61 |
| 2002/0065517 A1 | 5/2002 | Paul |
| 2002/0077630 A1 | 6/2002 | Lin |
| 2002/0111630 A1 | 8/2002 | Ralph et al. |
| 2003/0105461 A1 | 6/2003 | Putnam |
| 2003/0105471 A1 * | 6/2003 | Schlapfer et al. ............. 606/104 |
| 2003/0199876 A1 | 10/2003 | Brace et al. |
| 2004/0015169 A1 | 1/2004 | Gause |
| 2004/0039387 A1 | 2/2004 | Gause et al. |
| 2004/0059335 A1 | 3/2004 | Weaver et al. |
| 2004/0068319 A1 | 4/2004 | Cordaro |
| 2004/0116931 A1 | 6/2004 | Carlson |
| 2004/0127896 A1 | 7/2004 | Lombardo et al. |
| 2004/0127904 A1 | 7/2004 | Konieczynski et al. |
| 2004/0167522 A1 | 8/2004 | Niederberger et al. |
| 2004/0181228 A1 | 9/2004 | Wagner et al. |
| 2004/0204712 A1 | 10/2004 | Kolb et al. |
| 2004/0204713 A1 | 10/2004 | Abdou |
| 2004/0220570 A1 | 11/2004 | Frigg |
| 2004/0236332 A1 | 11/2004 | Frigg |
| 2004/0254579 A1 | 12/2004 | Buhren et al. |
| 2005/0010226 A1 * | 1/2005 | Grady et al. ..................... 606/69 |
| 2005/0043736 A1 * | 2/2005 | Mathieu et al. ................. 606/73 |
| 2005/0049594 A1 * | 3/2005 | Wack et al. ..................... 606/69 |
| 2005/0080421 A1 | 4/2005 | Weaver et al. |
| 2005/0107796 A1 | 5/2005 | Gerlach et al. |
| 2005/0124994 A1 | 6/2005 | Berger et al. |
| 2005/0149027 A1 | 7/2005 | Campbell et al. |
| 2005/0154392 A1 * | 7/2005 | Medoff et al. .................. 606/69 |
| 2005/0159753 A1 | 7/2005 | Kitchens |
| 2005/0165400 A1 * | 7/2005 | Fernandez ...................... 606/69 |
| 2005/0192576 A1 | 9/2005 | Michelson |
| 2005/0246021 A1 | 11/2005 | Ringeisen et al. |
| 2006/0058798 A1 | 3/2006 | Roman et al. |
| 2006/0149263 A1 * | 7/2006 | Newcomb et al. .............. 606/73 |
| 2006/0200134 A1 | 9/2006 | Freid et al. |
| 2006/0235399 A1 * | 10/2006 | Carls et al. ...................... 606/69 |
| 2006/0235405 A1 | 10/2006 | Hawkes |
| 2007/0027230 A1 | 2/2007 | Beyar et al. |
| 2007/0055257 A1 | 3/2007 | Vaccaro et al. |
| 2007/0088362 A1 | 4/2007 | Bonutti et al. |
| 2007/0162016 A1 * | 7/2007 | Matityahu ....................... 606/69 |
| 2007/0173843 A1 | 7/2007 | Matityahu |
| 2008/0300637 A1 * | 12/2008 | Austin et al. .................. 606/290 |
| 2008/0306550 A1 | 12/2008 | Matityahu |

* cited by examiner

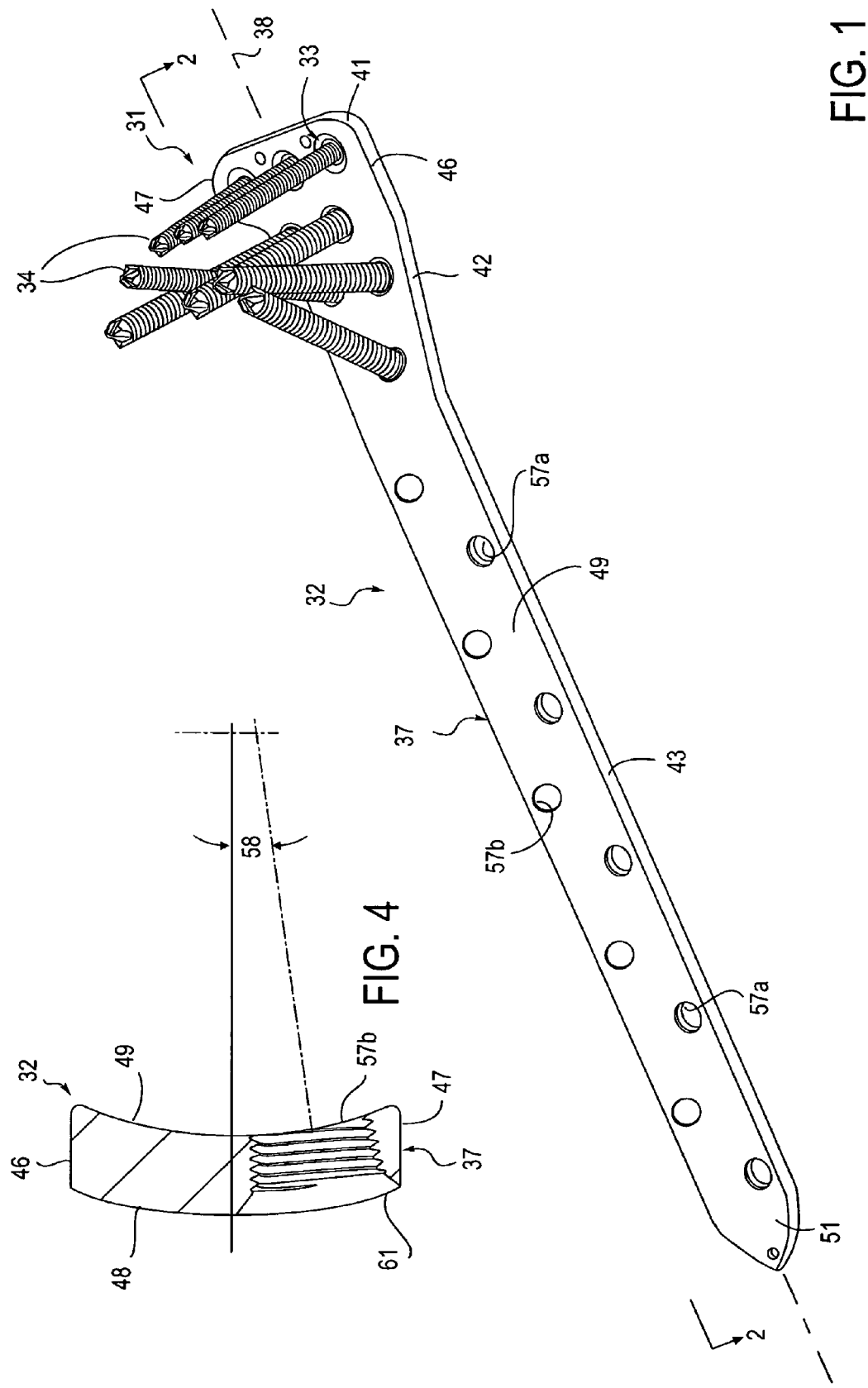

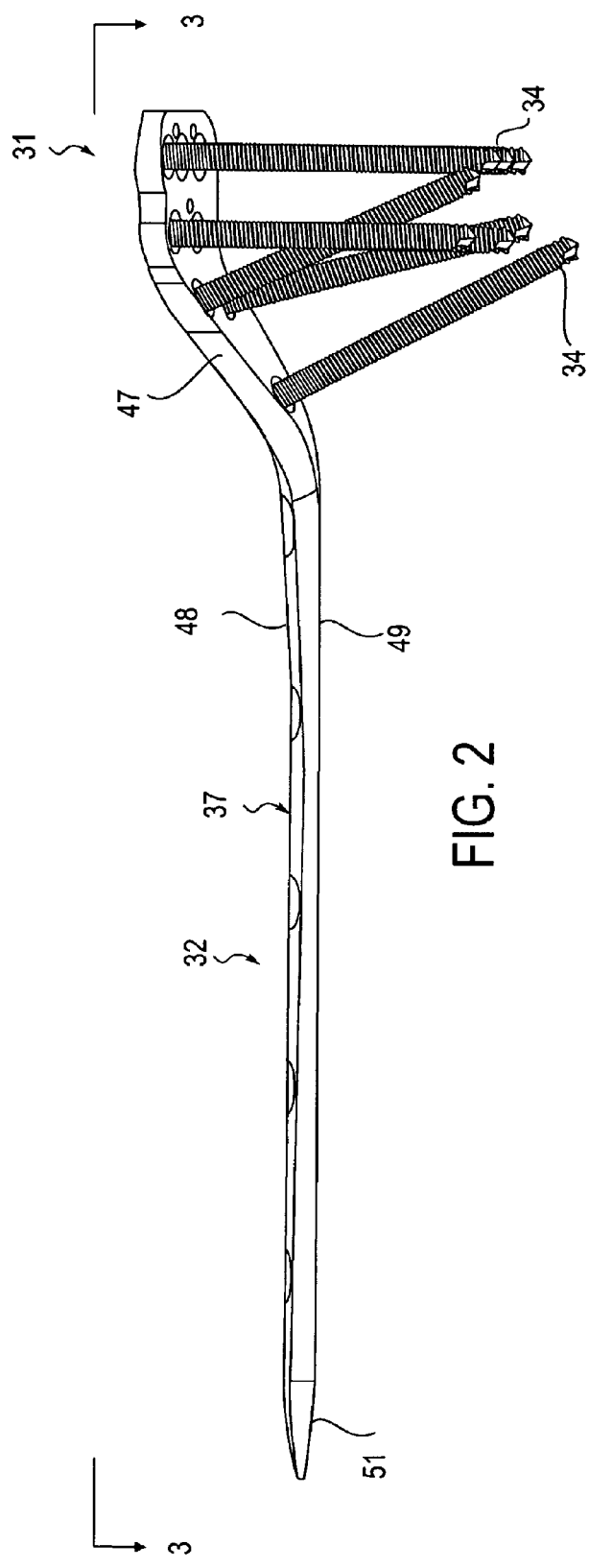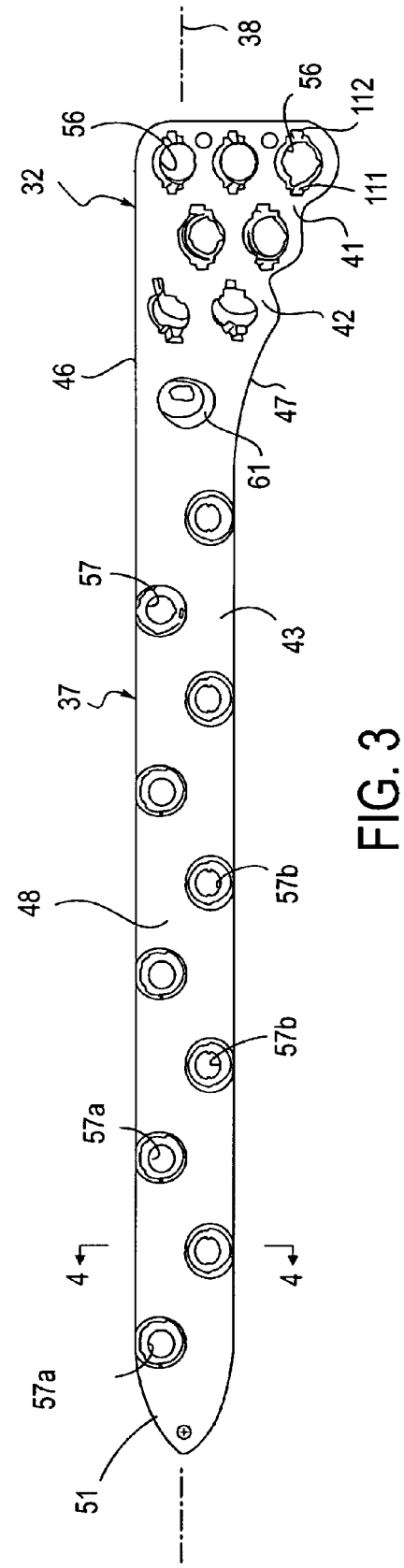

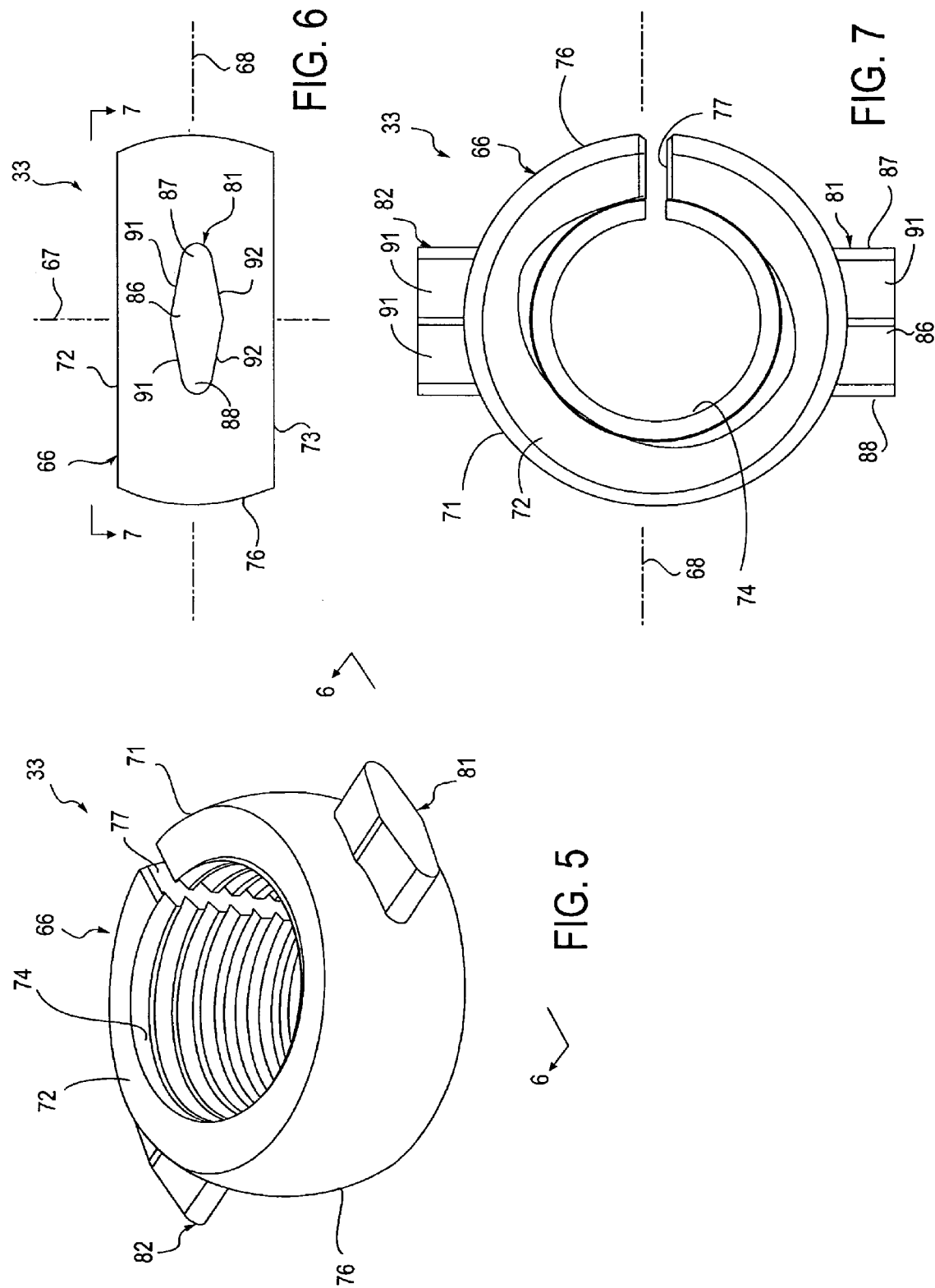

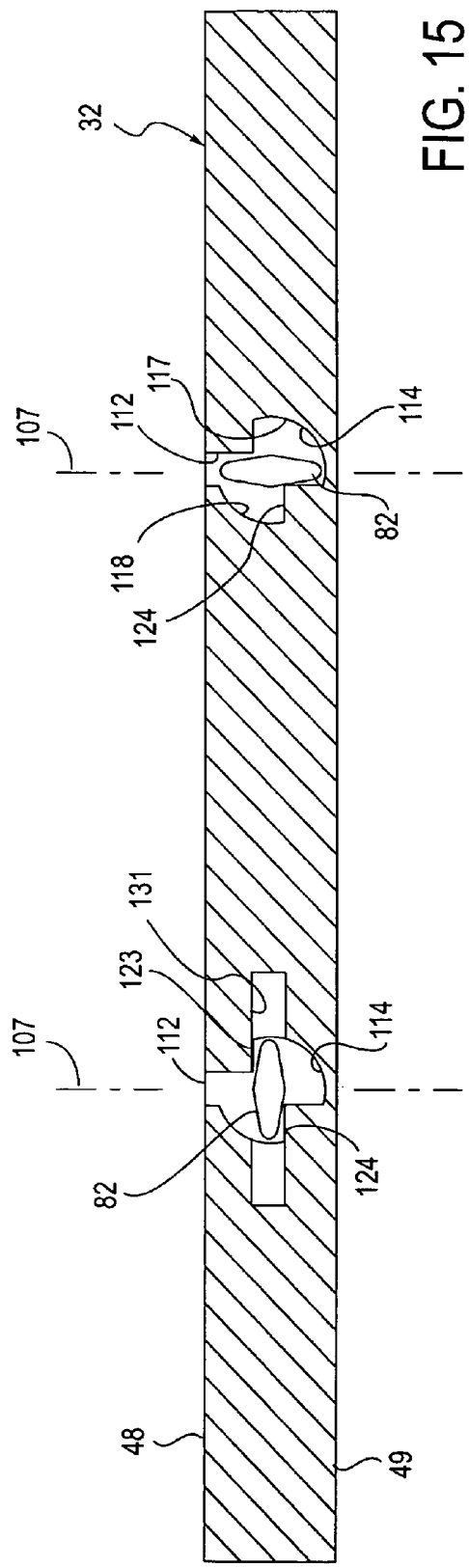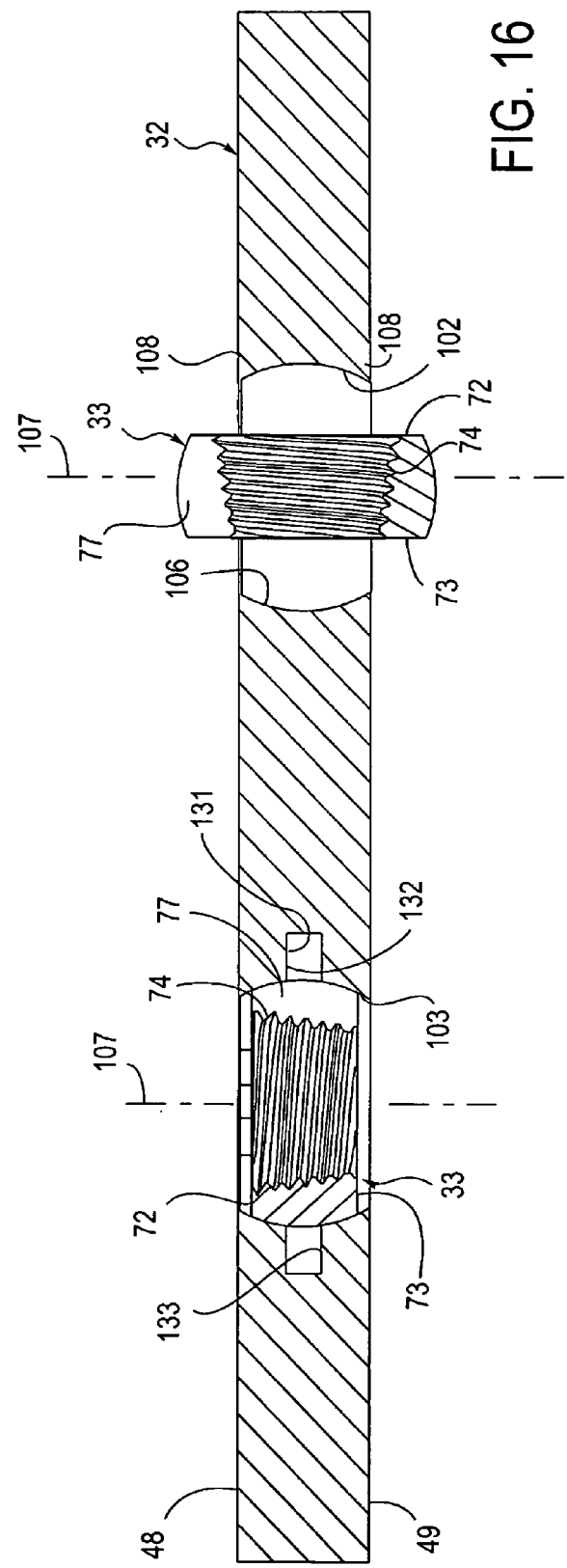

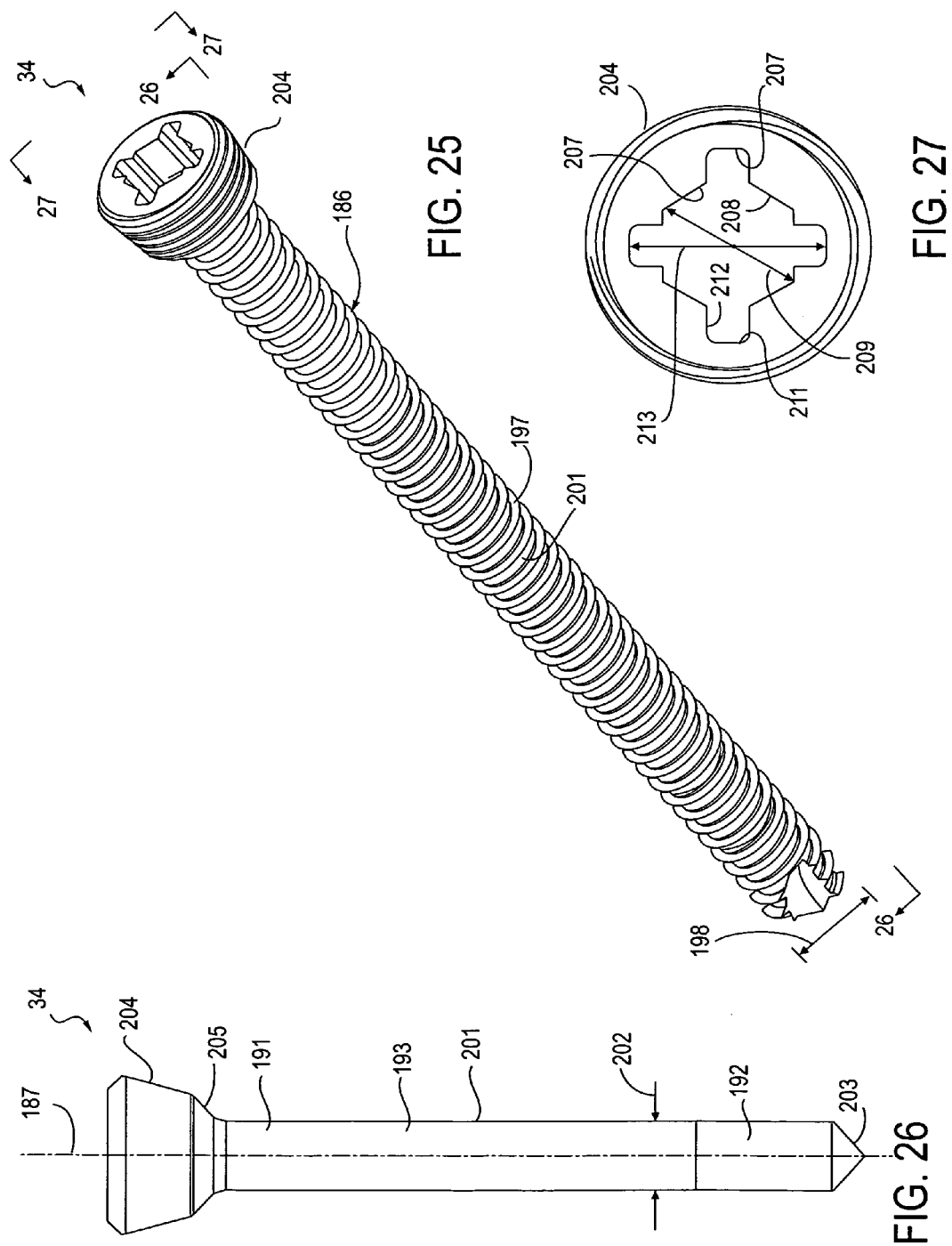

BONE ATTACHMENT SCREW

CROSS REFERENCE TO RELATED APPLICATION

This application claims priority to U.S. provisional patent application Ser. No. 60/730,491 filed Oct. 25, 2005, the entire content of which is incorporated herein by this reference.

SCOPE OF THE INVENTION

The present invention relates to a bone fastening assembly, and more particularly to a bone locking plate and screws for fastening the plate to a mammalian body.

BACKGROUND

The skeletal system includes many long and flat bones which, for example with respect to a human body, extend from the human torso. These bones include the pelvis, spine, humerus, radius, ulna, bones of the hand, femur, tibia, fibula, and bones of the foot. These bones are particularly exposed to trauma from accidents which can cause complex and devastating fractures of the bones. In particular, the femur, tibia, and humerus are often fractured close to the hip joint, knee joint, ankle joint, shoulder joint, and elbow joint. Frequently, the distal and/or proximal portions of the long bone that is fractured must be secured to a bone plate with the major fracture fragments aligned anatomically.

Pins, bone plates and bone screws have been used for repairing fractured bones. The plates are usually placed longitudinally along the periphery of the long bone and have holes or openings through which screws may be inserted into the long bone transversely. When the fracture of a long bone occurs at its end, many bone fragments often result and must be reconnected. The bone plate is ideally placed distal and/or proximal to the fractured area to permit securing of these fragments.

Bone plates that are contoured to the anatomy of a bone have been provided for the fixation of bone fractures and osteotomy fixation. Such bone plates typically either allow for rigid locking of the screw into the plate hole in only one direction or allow the screw to be directed in any plane and then locked. If the plate holes allow for only one direction of insertion, the optimal position of the screw in the plate may not allow for fracture fragment capture by the screw. If the plate holes allow the screw to be directed in a multidirectional manner, screws may capture bone fragments not otherwise captured. Further, currently provided bone plates with multi-directional screw locking mechanisms in the plates do not offer the ability to use the orientation of the screw to align the bone fragments, as may be done with a currently-provided bone plate having a screw fixed or locked in a single direction.

Locking plates have recently been developed for use in spinal and long bone applications. Such plates have bushings that are internally threaded and externally smooth and circular so as to pivot within the bone plate openings and thus allow for multidirectional bone screw insertion. Unfortunately, when locking a bone screw into one of these plates, the pivot movement of the bone screw relative to the bone plate is hindered by the friction of the smooth outer surface of the bushing and the radial force applied by the conical screw head to the internally-threaded surface of the bushing that causes the bushing to expand. The force applied to the screw in the frontal and sagittal planes of the body may cause a loss of stability between the screw head and the plate.

There is a need for a new bone fastening assembly that overcomes the foregoing disadvantages.

SUMMARY OF THE INVENTION

A bone fastening assembly for use with a screw and including a bone plate and a bushing having a bore adapted for receiving the screw is provided. The bone plate has a substantially planar portion and is provided with a hole in the portion for receiving the bushing. The portion of the bone plate and the bushing are cooperatively configured for providing pivotal movement of the bushing within the hole about a pivot axis and restricting the pivot axis to a plane extending in the portion of the bone plate. A new bone attachment screw for use with the bone fastening assembly is provided.

BRIEF DESCRIPTION OF THE DRAWINGS

FIG. 1 is a bottom perspective view of a bone fastening assembly of the present invention.

FIG. 2 is a posterior side elevational view of the bone fastening assembly of FIG. 1 taken along the line 2-2 of FIG. 1.

FIG. 3 is a top plan view of the bone fastening assembly of FIG. 1, with the bushings and screws removed, taken along the line 3-3 of FIG. 2.

FIG. 4 is a cross-sectional view of the bone fastening assembly of FIG. 1 taken along the line 4-4 of FIG. 3.

FIG. 5 is a perspective view of a bushing of the bone fastening assembly of FIG. 1.

FIG. 6 is an end view of the bushing of FIG. 5 taken along the line 6-6 of FIG. 5.

FIG. 7 is a top plan view of the bushing of FIG. 5 taken along the line 7-7 of FIG. 6.

FIG. 15 is a cross-sectional view of the portion of the bone plate of FIG. 14 taken along the line 15-15 of FIG. 14.

FIG. 16 is a cross-sectional view of the portion of the bone plate of FIG. 14 taken along the line 16-16 of FIG. 14.

FIG. 25 is a perspective view of a bone screw of the present invention.

FIG. 26 is a side elevational view, with the helical threads removed, of the inner diameter of the bone screw of FIG. 25 taken along the line 26-26 of FIG. 25.

FIG. 27 is an end view of the bone screw of FIG. 25 taken along the line 27-27 of FIG. 25.

DESCRIPTION OF THE INVENTION

Figure 8:
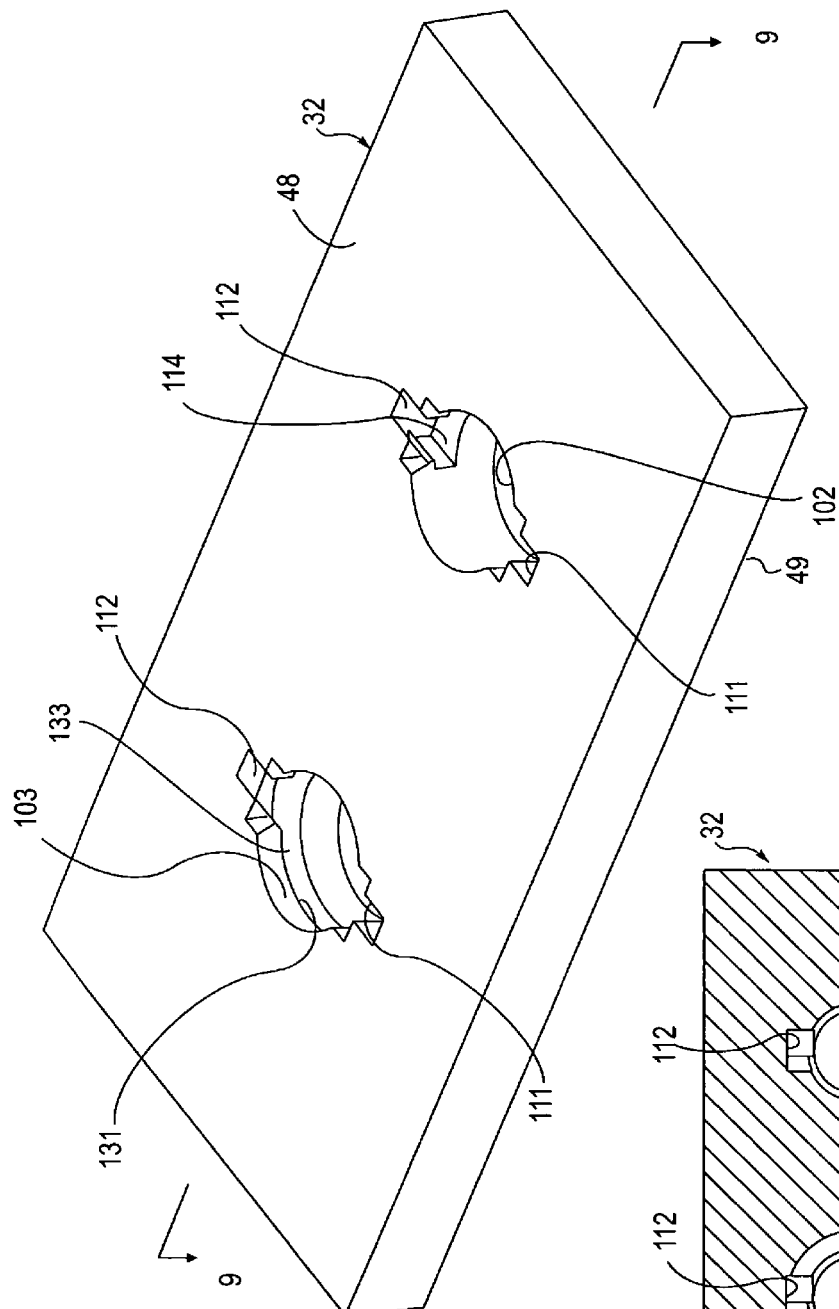
FIG. 8 is a perspective view of a portion of the bone plate of the bone fastening assembly of FIG. 1 illustrating first and second embodiments of a screw hole in the bone plate for receiving the bushing of FIG. 5.
Figure 9:
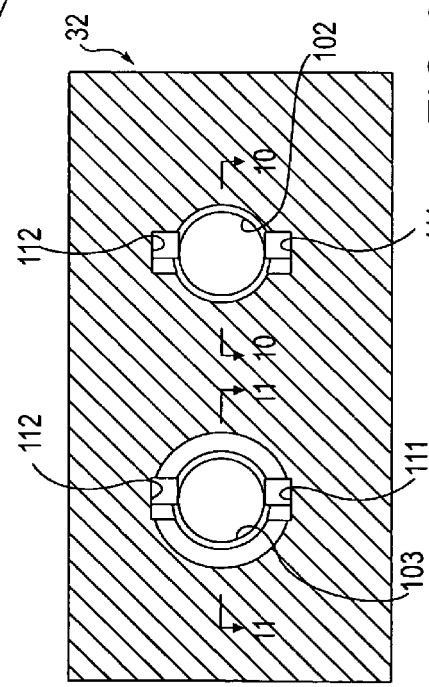
FIG. 9 is a cross-sectional view of the portion of bone plate of FIG. 8 taken along the line 9-9 of FIG. 8.

In general, the present invention relates to a bone fastening assembly 31 that includes a bone locking plate or bone plate 32 and a plurality of adjustable attachment components or bushings 33 and a plurality of bone or attachment screws 34 for use with the bone plate 32. The angle of a bushing 33 relative to the bone plate 32 maybe manipulated during certain surgeries so that an accompanying screw 34 extends into the bone being treated in a desirable orientation. This orientation can be constrained in one plane. For example, the axis about which the bone screw pivots can be constrained to a single plane, such as the plane of the bone plate, and variable in another plane, for example the bone screw can pivot about such pivot axis in a plane extending perpendicular to the plane of the bone plate. Although the bone fastening assembly 31 can be used with any suitable bone of a mammalian body, for example a long bone such as the humerus, radius, ulna, femur or fibula, bone fastening assembly 31 is described and illustrated herein for use with a tibia.

Bone plate 32 is formed from an elongate body 37 made for any suitable material such as a composite material or metal and is preferably made from stainless steel or titanium. The elongate body 37 extends along a longitudinal centerline 38 and is formed with a head 41, a neck 42 and a shaft 43 (see FIGS. 1-3). The head 41 of the bone plate is anatomically contoured to the end of the long bone being treated, in this instance the end of the tibia. The shaft 43 and the neck 42, located between the head 41 and the shaft 43, are also anatomically shaped relative to the tibia. The elongate body 37 has an anterior or front 46 and a posterior or back 47, shown most clearly in FIG. 3, and an outer surface or face 48 and an inner or bone-facing surface 49 extending between the anterior 46 and the posterior 47. A tapered distal end 51 is provided on the shaft 43.

Bone plate 32 is provided with a plurality of apertures or holes for directly or indirectly receiving bone screws 34. In this regard, some or all of such holes can be configured to receive a bushing 33 so as to indirectly receive a bone or attachment screw 34, and some or all of such holes can be threaded so as to directly receive a bone screw 34. It is appreciated that any combination of threaded and bushing—receiving holes can be provided. In the illustrated tibia bone plate 32, a plurality of holes or apertures 56 are provided in head 41 and neck 42 of the elongate body 37 and a plurality of threaded apertures or holes 57 are provided in shaft 43 of the body 37.

Threaded holes 57 in shaft 43 can be arranged in any suitable configuration or array. In one embodiment, shaft 43 is provided with a first plurality of holes 57a longitudinal spaced-apart along one side of centerline 38 and a second plurality of holes 57b longitudinal spaced-apart along the other side of centerline 38 (see FIGS. 1 and 3). As such, the first plurality of holes 57a is longitudinally offset relative to the second plurality of holes 57b and, more preferably, holes 57a and 57b are interspersed at approximate equal longitudinal distances from each other along the length of the shaft 43. Each of the holes 57 is preferably threaded in a direction inclined toward the centerline 38 of the shaft 43. More preferably, the bone plate apertures in the shaft 43 have a concavity away from the bone being treated, that is the apertures 57 are tapered inwardly from outer face 48 to inner face 49 of the bone plate 38 as shown most clearly in FIG. 4. The angle of inclination 58, shown in FIG. 4, can range from 3 to 15 degrees and preferably approximately 6 degrees. Shaft 43 is arcuate in cross section relative to centerline 38, as shown in FIG. 4, and more specifically is concave at inner face 49 and convex at outer face 48. Each of the bores 47 is preferably formed with an angular or tapered surface 61 which ramps inwardly from outer surface 48 toward the centerline of the hole 57 as shown in FIG. 4 for urging the leading end of a screw toward the center of the bore 57 during placement of the screw in a body of a patient. When outer surface 48 of shaft 43 is viewed in plan, as shown in FIG. 3, the entrance or ramped surface 61 of at least some of holes 57 is oblong shaped or oval shaped relative to the centerline of the corresponding hole 57. The long dimension of such oblong-shaped ramps is preferably aligned with or parallel to the longitudinal centerline 38 of the shaft 32. The number and location of screw holes 57 having an oblong-shaped or oval-shaped ramped surface 61 can vary.

Each of bushings 33 is made from a cylindrical or tubular body 66, illustrated in FIGS. 5-7, that is formed from any suitable material such as a composite material or a metal and is preferably made from stainless steel or titanium. The tubular bodies 66 of bushings 33 are sized for placement in apertures 56. The tubular body 66 has an axial centerline 67 and a transverse centerline 68, as shown in FIG. 6. The tubular body 66 has an outer annular wall 71 with top and bottom planar surfaces 72 and 73 so as to be substantially planar in conformation. An internally-threaded bore 74 is formed by wall 71 and extends along vertical centerline 67. The threads of bore 74 preferably taper inwardly toward the axial centerline 67 as they extend from top surface 72 to bottom surface 73 of the bushing 33. The body 66 is substantially cylindrical along the centerline 67. Outer surface 76 of annular wall 71 extends around the centerline 67 and is longitudinally convex relative to the centerline so as to have an outwardly-bowed arcuate shape. An opening, gap or slit 77 extends between threaded bore 74 and outer surface 76 along the transverse centerline 78 and in a direction parallel to the axial centerline 67.

First and second transversely-aligned pins 81 and 82 extend horizontally outwardly from opposite sides of annular wall 71. Preferably, each of the pins 81 and 82 is vertically centered relative to top and bottom surfaces 72 and 73 so as to protrude from the outermost portion of the convex outer surface 76 and extend in a direction perpendicular to vertical centerline 67. The first and second pins 81 and 82, which can also be referred to as outcrops, protuberances, projections, bulges, knobs, shelves or tabs, are each preferably in the form of a wing. Each of such wings 81 and 82 can be of any suitable shape and in one embodiment, when viewed from its end as shown in FIG. 6, tapers inwardly in a forward direction from its center 86 to a forward winged portion 87 and tapers in a rearward direction from its center 86 to a rearward winged portion 88. Each of the winged portions is formed from a downwardly-sloped ramped top surface 91 and an upwardly-sloped ramped bottom surface 92. Each of the surfaces 91 and 92 is inclined at an angle relative to horizontal centerline 68 of the tubular body 66.

First and second embodiments of apertures 56 suitable for use in bone plates 32 are illustrated in FIGS. 8-16. A portion of bone plate 32 is shown schematically in FIG. 8 and, as illustrated therein, is substantially planar and thus extends in a plane. In general, aperture 102 shown in the right portion of bone plate 32 restricts the axis about which bushing 33 pivots to a line extending in the plane of the bone plate 32. Aperture 103 shown in the right portion of bone plate 32 restricts the pivot axis of the bushing to the plane of the bone plate 32.

Figure 12:
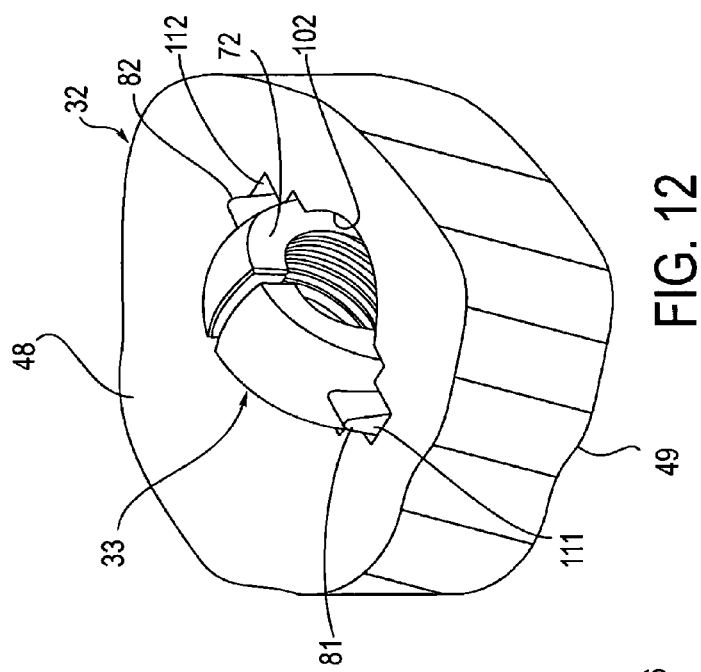
FIG. 12 is a perspective view of the bushing of FIG. 5 in a vertical position entering one of the screw holes in the portion of the bone plate of FIG. 8.
Figure 10:
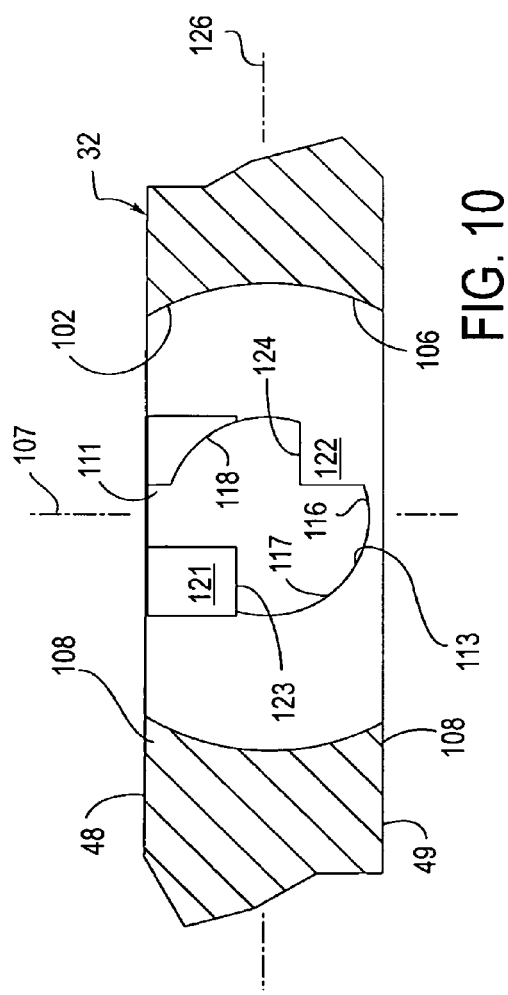
FIG. 10 is a cross-sectional view of the first embodiment of the screw hole in the portion of the bone plate of FIG. 8 taken along the line 10-10 of FIG. 9.
Figure 11:
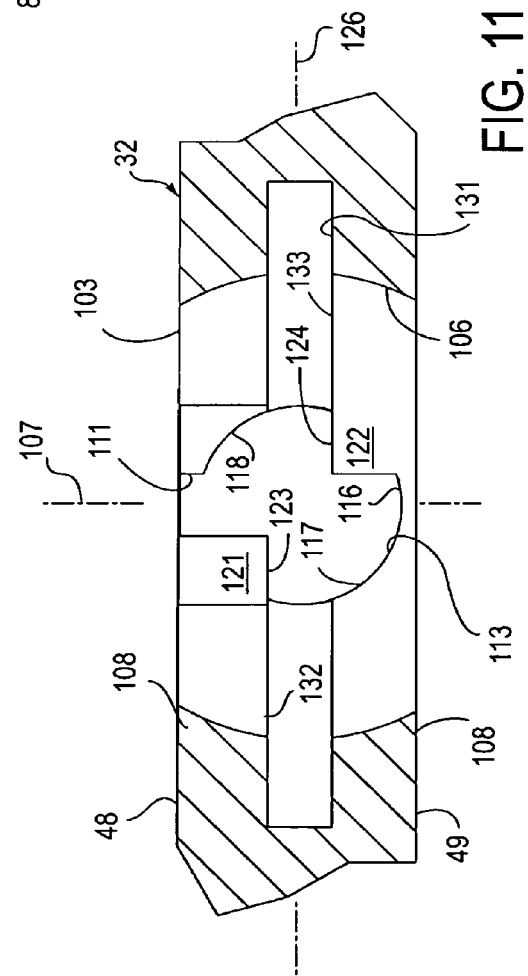
FIG. 11 is a cross-sectional view of the second embodiment of the screw hole in the portion of the bone plate of FIG. 8 taken along the line 11-11 of FIG. 9.
Figure 13:
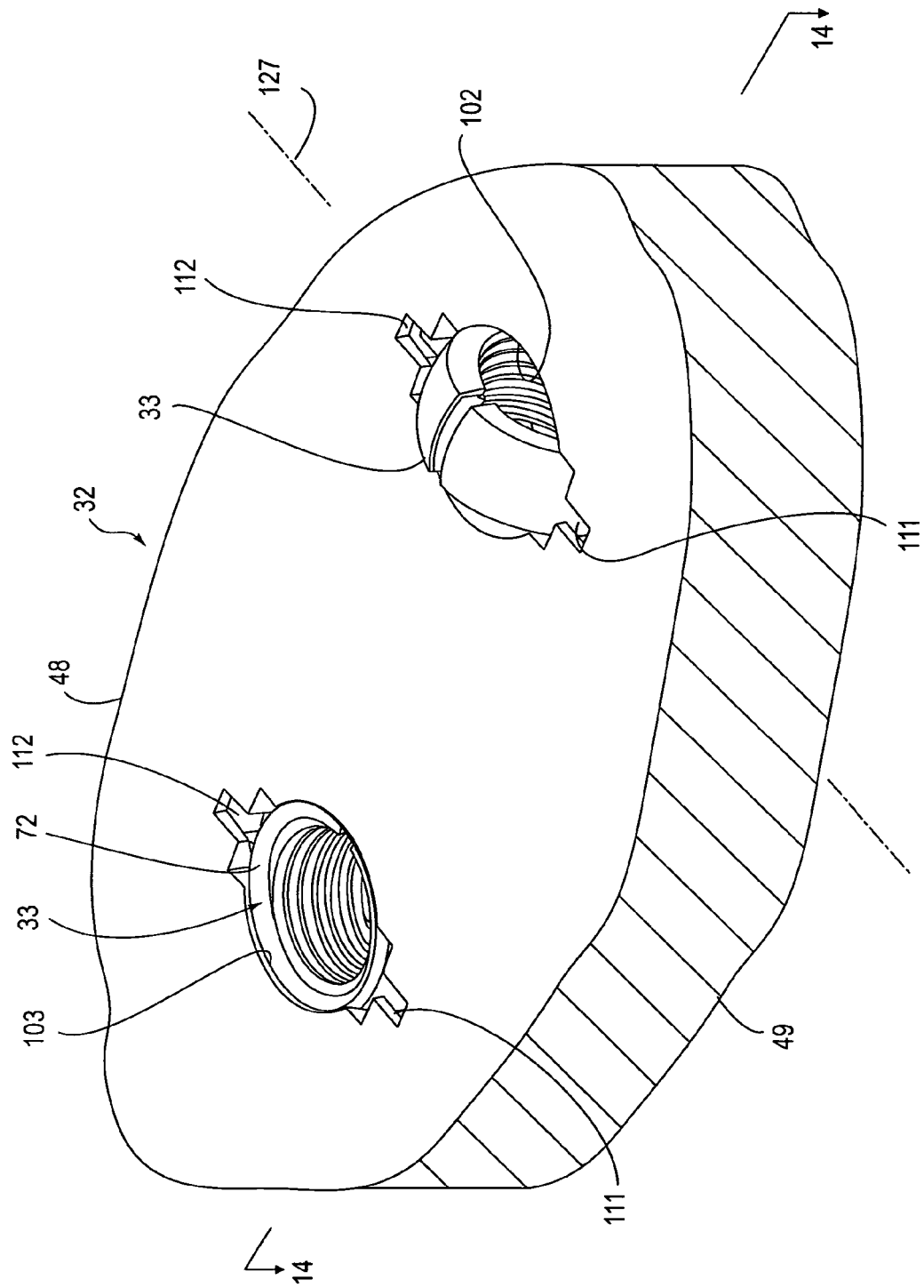
FIG. 13 is a perspective view, similar to FIG. 12, of a first bushing fully seated in a vertical position in the first embodiment of the screw hole in the portion of the bone plate of FIG. 8 and a second bushing fully seated and rotated to a horizontal position n in the second embodiment of the screw hole in the portion of the bone plate of FIG. 8.
Figure 14:
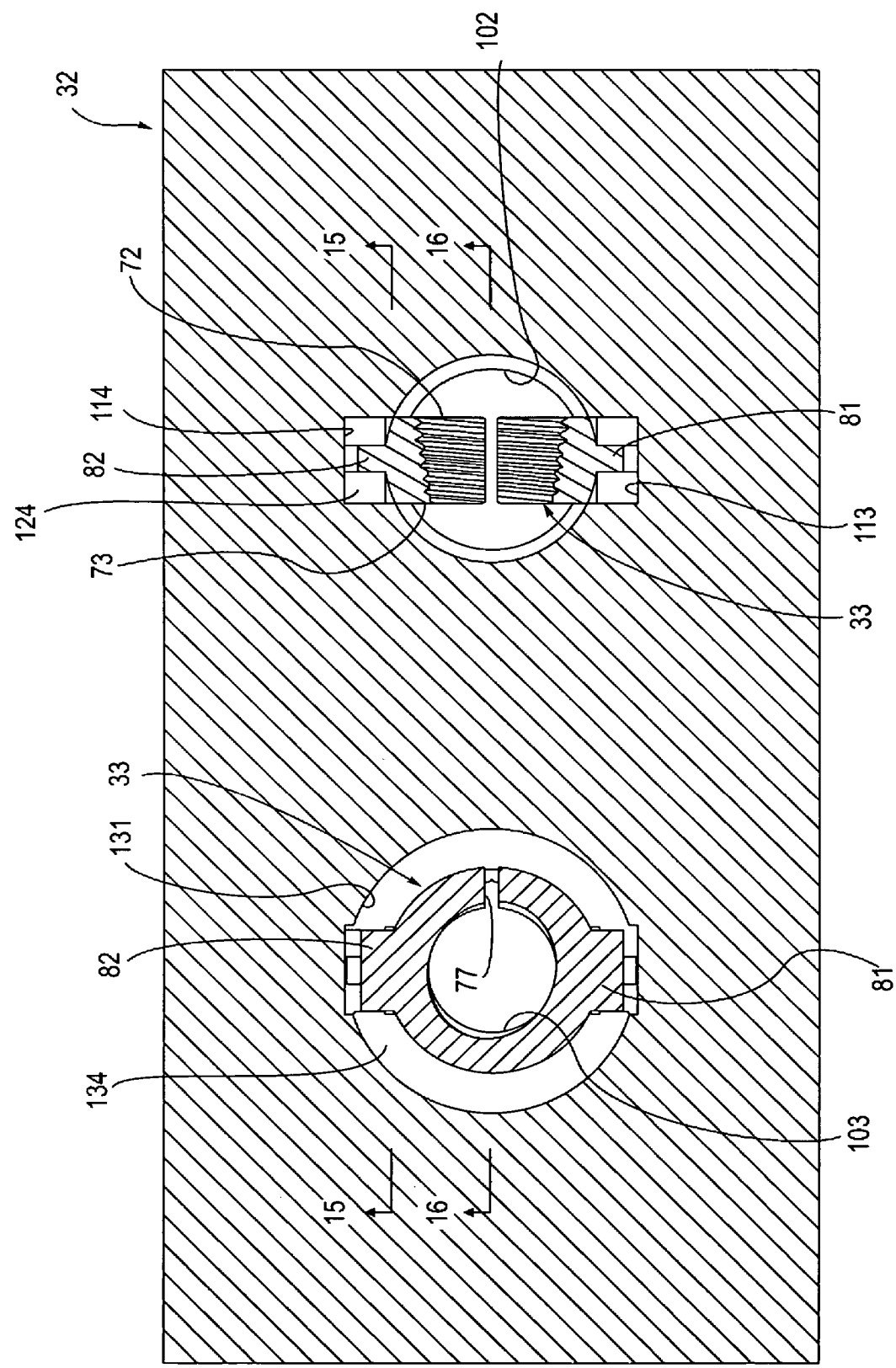
FIG. 14 is a cross-sectional view of the portion of the bone plate of FIG. 13 taken along the line 14-14 of FIG. 13.
Figure 17:
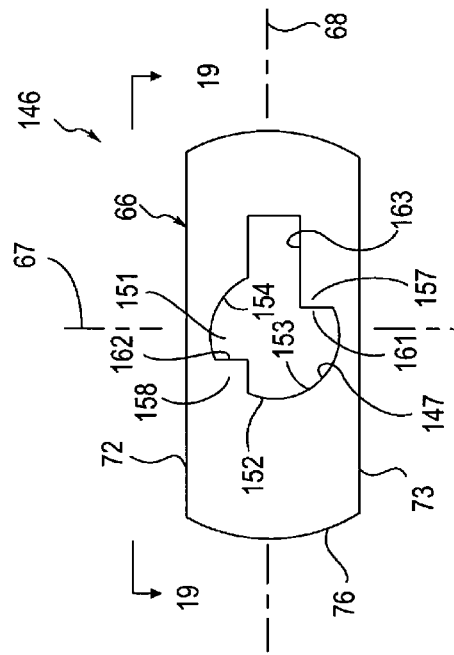
FIG. 17 is a perspective view of another embodiment of a bushing of the bone fastening assembly of the present invention.
Figure 18:
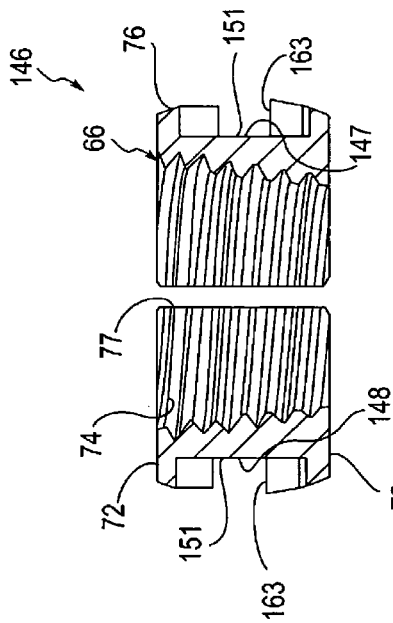
FIG. 18 is an end view of the bushing of FIG. 17 taken along the line 18-18 of FIG. 17.
Figure 19:
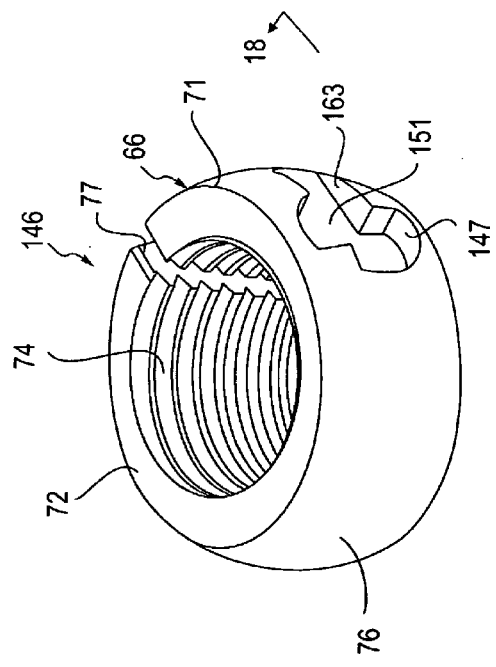
FIG. 19 is a top plan view of the bushing of FIG. 17 taken along the line 19-19 of FIG. 18.
Figure 20:
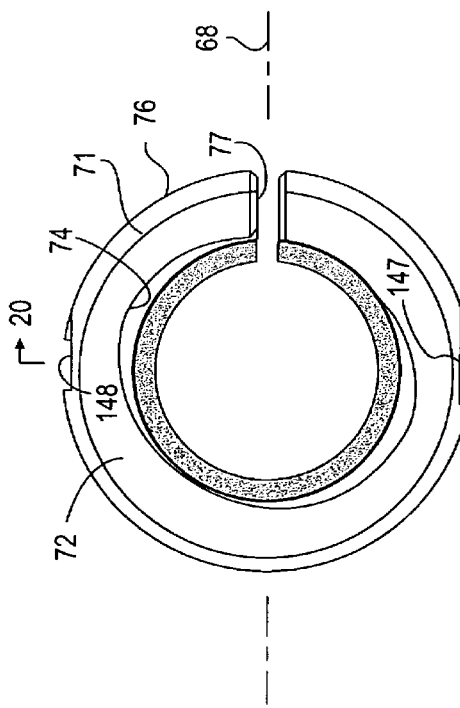
FIG. 20 is a cross-sectional view of the bushing of FIG. 17 taken along the line 20-20 of FIG. 19.
Figure 21:
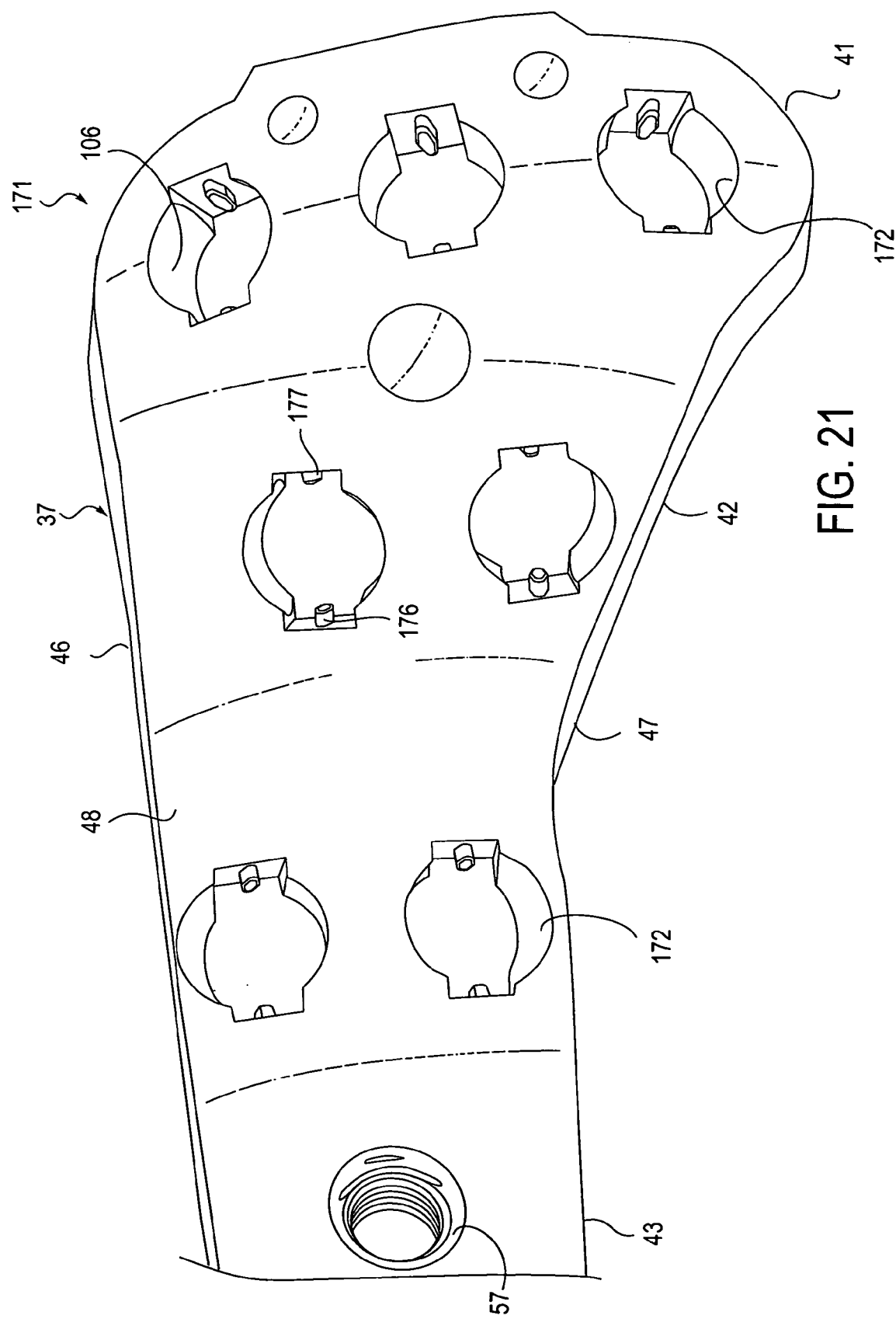
FIG. 21 is a perspective view of a portion of a bone plate of the present invention for use with the bushing of FIG. 17.
Figure 22:
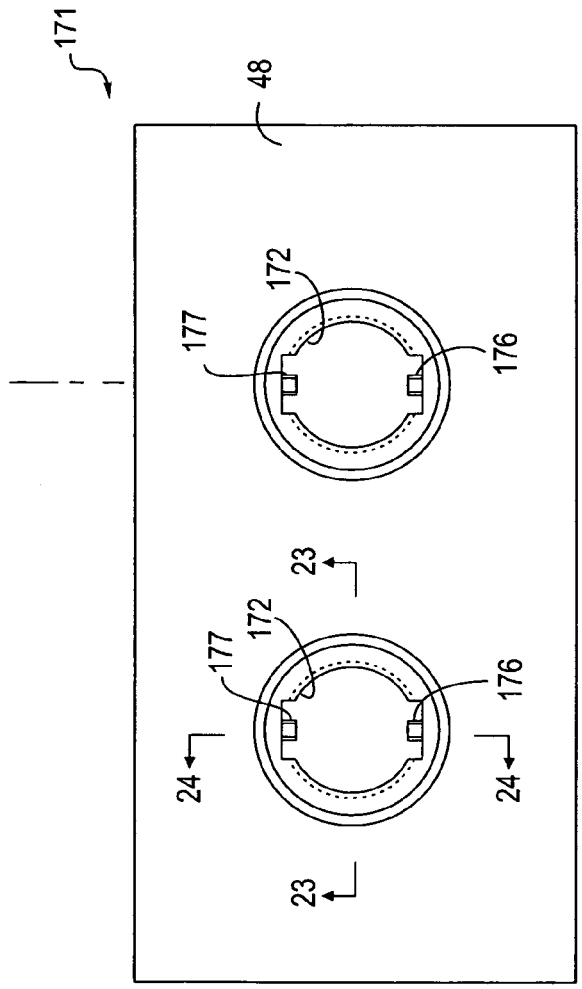
FIG. 22 is a top plan view of a portion of the bone plate of FIG. 21.
Figure 24:
FIG. 24 is a cross-sectional view of the bone plate of FIG. 21 taken along the line 24-24 of FIG. 22.
Figure 23:
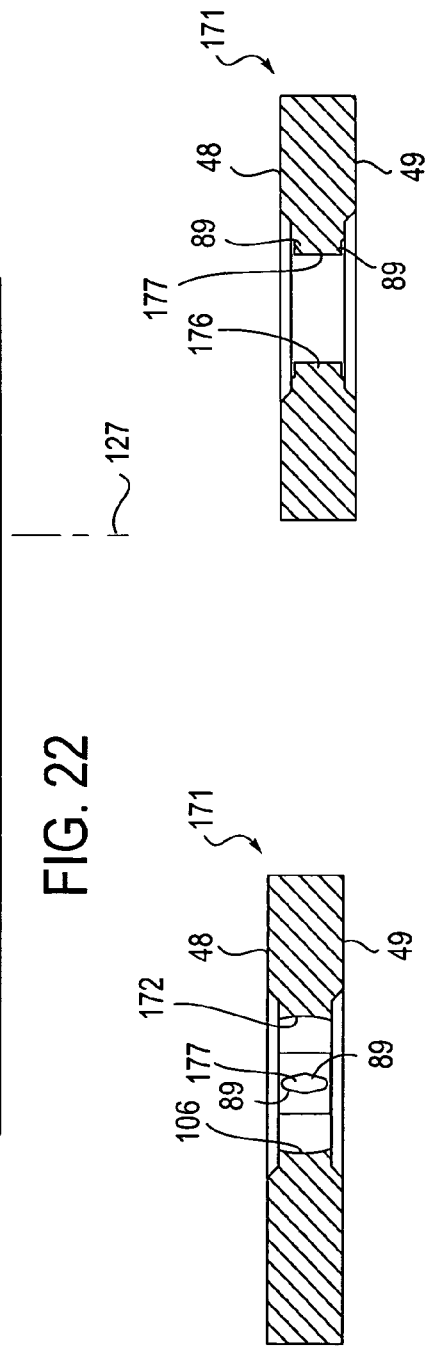
FIG. 23 is a cross-sectional view of the bone plate of FIG. 21 taken along the line 23-23 of FIG. 22.

The bore of aperture 102 is formed with an internal surface 106, shown most clearly in FIGS. 8, 10 and 16, that is centered on the vertical centerline 107 of the aperture 102 and is arcuate and preferably concave relative to the centerline 107. More preferably, the arcuate shape of surface 106 approximates the arcuate shape of bushing outer surface 76. Bone plate 32 is provided with a circumferentially-extending ridge 108 around each of the upper and lower ends of the aperture 102 adjacent respective outer and inner faces 48 and 49 of the bone plate 32. A niche, gap, slit or slot extends through outer face 48 of the bone plate 32 on opposite sides of the entrance of aperture 102. Such first and second slots 111 and 112 are sized to receive respective first and second wings 81 and 82 when bushing 33 is disposed in a vertical position, as illustrated in FIG. 12, with respect to the aperture 102. The slots 111 and 112 serve as entrances to respective first and second internal recesses 113 and 114 extending through at least a portion of internal surface 106 at opposite sides of aperture 102, as shown most clearly in FIGS. 10, 14 and 15. Each such recess is formed with a bottom surface 116 that is part of a ramped, arcuate lower surface 117 extending upwardly and inwardly from the bottom of the recess. A similar ramped, arcuate upper surface 118 is diametrically opposed to surface 117 for forming a portion of the other side of the recess. The lower and upper ramped surfaces 117 and 118 end at respective upper and lower shoulders 121 and 122, which have respective upper and lower limiting surfaces 123 and 124 that extend parallel to horizontal centerline 126 of the portion of the bone plate 32 in the vicinity of the aperture 102 (see FIG. 10).

The placement of a bushing 33 and aperture 102 will now be described. The bushing 33 is initially placed in a vertical position relative to the bone plate 32, as illustrated in FIG. 12, and first and second wings 81 and 82 of the bushing aligned with first and second slots 111 and 112 of the bone plate. The bushing 33 is then vertically inserted into the aperture 102, with the vertically aligned wings 81 and 82 traveling through respective slots 111 and 112 into respective recesses 113 and 114. The leading edge or winged portion 87 of each wing 81 and 82 engages bottom surface 116 of the recess to limit the insertion travel of the bushing. Thereafter, the bushing 33 is rotated about a pivot axis 127, shown in FIG. 13, that extends horizontally through the bushing and the centers of first and second wings 81 and 82. During such rotation, the leading winged portion 87 of each of the wings 81 and 82 travels along the lower ramped surface 117 forming first and second recesses 113 and 114. Concurrently, the concave internal surface 106 of bone plate 32 engages the convex outer surface 76 of the bushing 33. Bone plate internal surface 106 has a radial dimension that is slightly smaller then the radial dimension of bushing outer surface 76 so as to exert a compressive radial force against the bushing as the bushing is rotated from its vertical position to its horizontal position within aperture 102. Slit 77 in the bushing permits elongate body 37 of the bushing to radially contract during such rotation. The cooperatively similar contours of aperture internal surface 106 and bushing outer surface 76 facilitate a smooth compression and contraction of the bushing 33. The seated bushing is under slight radial compression from the engagement of the bone plate internal surface 106 with the bushing outer surface 76.

Once bushing 33 has been so placed within aperture 102, the bushing can rotate or pivot through a limited range of motion about pivot axis 127, which passes through the centers of first and second recesses 113 and 114. The capture of first and second wings 81 and 82 of the bushing within the respective recesses 113 and 114 fixes pivot axis 127 with respect to bone plate 32. The engagement of top ramped surface 91 or bottom ramped surface 92 of the bushing with respective upper limiting surface 123 or lower limiting surface 124 within the bone place 32 limits the range of pivotably motion of the bushing within the bone plate in one direction. Preferably the pivotably motion is limited such that the entire convex outer surface 76 of the bushing is recessed within aperture 102 and continuously and fully engaged by the concave internal surface 106 of the bone plate. The angle of inclination of ramped surfaces 91 and 92 of the bushing can be varied to determine the range of pivotably motion of the bushing within the bone plate. In this manner, a variety of bushings with differently configured first and second wings 81 and 82 can be provided for easily selecting the desired range of pivotably motion of the bushing and thus the bone screw 34 utilized therewith. It is appreciated that the spacing between upper and lower limiting surfaces 123 and 124 relative to horizontal centerline 126 in the bone plate 32 can also be adjusted to change the range of pivotal motion of a bushing 33 within the bone plate.

Upper and lower ridges 108 of bone plate 32 restrict bushing 33 from inadvertently separating from the bone plate during placement and manipulation of the bushing within the bone plate and during attachment of the bone plate to a bone of a patient. In this regard, bone plate 32 has a thickness in the vicinity of each aperture 102 and bushing 33 and a thickness between top and bottom surfaces 72 and 73 that is less than the thickness of the bone plate in the vicinity of the aperture 102. After insertion of the bushing 33 into the bone plate 32, upper ridge 108 can be optionally punched or otherwise narrowed (not shown) so as to restrict the bushing from being rotated to a vertical position and thus removed from the bone plate 32. Alternatively, or in addition, outer face 38 of the bone plate 32 can be punched at the entrance of first and second slots of 111 and 112 to similarly restrict removal of the bushing 33 from bone plate 32.

Aperture 103 permits pivot axis 127 to be rotated in the plane of bone plate 32 about an axis extending perpendicular to such plane to a desired location so as to select the pivot plane in which the related bone screw 34 moves relative to the bone plate. The aperture 103 is formed from bone plate 32 in a manner substantially similar to aperture 102 and like reference numerals have been used to describe like features of apertures 103 and 102 and bone plate 32. As shown most clearly in FIG. 11, aperture 103 includes a groove 131 extending at least partially about the vertical centerline 107 of the aperture and preferably entirely around the circumference of the aperture. The groove 131 extends in the plane of the portion of the bone plate 32 in the vicinity of aperture 103 and is preferably formed with an upper surface 132 coplanar with upper limiting surface 123 and a lower surface 133 coplanar with lower limiting surface 124. Planar upper and lower surfaces 132 and 133 extend parallel to each other.

Bushing 33 is inserted into aperture 103 in the same manner discussed above with respect to the insertion of the bushing 33 into aperture 102. Once the bushing has been rotated to a horizontal position relative to the bone plate 32, as illustrated in FIGS. 13-16, the bushing can be rotated within aperture 103 about an axis extending perpendicular to the plane of the bone plate so that the diametrically-aligned wings 81 and 82 of the bushing are in the desired portions of annular groove 131. Such portions of the groove 131 serve as transversely-aligned or diametrically-aligned recesses for receiving the wings 81 and 82. Upper and lower internal surfaces 132 and 133 of the bone plate can serve as limiting surfaces, like limiting surfaces 123 and 124, for limiting the range of pivotal motion of the bushing 33 about the pivot axis 127.

In one preferred embodiment of bone plate 32, shown in FIG. 3, the three apertures 56 along the proximal end of head 41, which accommodate the three end screws in head 41, are formed like aperture 102. As shown in FIG. 3, first and second slots 111 and 112 of these three apertures 56, and thus first and second recesses 113 and 114 thereunder, are aligned parallel to each other and to the longitudinal centerline 38 of the bone plate such that pivot axes 127 of the bushings 33 placed within such three apertures 56 will extend parallel to each other so as to restrict pivotal movement of such bushings, and the related bone screws 34, to side to side movement in a common plane extending perpendicular to the head 41. The remainder of the apertures 56 in the head 41 and neck 42 of the bone plate 32 can be formed like apertures 102 or 103 or any combination thereof.

A plurality of mechanisms is carried by bone plate 32 for receiving a respective plurality of screws 34 and restricting pivotably movement of the screws 34 relative to the bone plate 32 about respective pivot axes 127. Each of such mechanisms can include a bushing 33 provided with first and second transversely-aligned pins 81 and 82 of any suitable configuration. The bone plate 32 can be furthered configured so that each of such mechanisms is provided with first and second transversely-aligned recesses, for example first and second recesses 113 and 114, for respectively receiving the first and second pins 81 and 82. It is appreciated that other embodiments can be provided, for example where one or more pins of any suitable type can be carried by the bone plate and first and second transversely-aligned recesses of any suitable type can be provided in the bushing. Further, other suitable pin and socket mechanisms can be provided with one or more pins provided on one of the bone plate and the bushing and one or more sockets provided on the other of the bone plate and the bushing. Such mechanisms can serve to restrict the pivot axis 127 of the bushing to a plane extending in the plane of the bone plate, or be more limiting so as to restrict the pivot axis 127 to a line extending to the plane of the bone plate. The plurality of mechanisms can be configured so that the pivot axes 127 are parallel to each other or disposed in any other suitable relationship to each other. The bone fastening assembly 31 can be configured to include cooperating engaging means which can be in the form of the mechanisms discussed above or any other suitable configuration for limiting the axis about which the bone screws pivot, whether such axis is in the plane of the bone plate or otherwise. It is appreciated that first and second pins 81 and 82 of bushing 33 and first and second recesses 113 and 114 in aperture 102 or groove 131 in aperture 103 are merely exemplary embodiments of the mechanisms and means described in this paragraph.

Other suitable embodiments of a bushing for use in a bone fastening assembly of the present invention can be provided. Bushing 146, illustrated in FIGS. 17-20, is substantially similar to bushing 33 and like reference numerals have been used to describe like elements of bushings 146 and 33. Instead of having first and second transversely-aligned pins, bushing 146 is provided with first and second transversely-aligned recesses 147 and 148 that are diametrically-aligned relative to annular wall 71 and extend substantially perpendicular to transverse centerline 68 of the bushing 146. In one embodiment, each of recesses 147 and 148 is formed by a planar base 151 extending perpendicular to a radian of the tubular body 66. The base 151 of recess 147 is preferably parallel of the base 151 of recess 148. Each of the recesses 147 and 148 can be shaped similar to first and second recesses 113 and 114 of bone plate 32 and thus include a bottom surface 152, which is part of a lower ramped surface 153, and an upper ramped surface 154, in each case similar to surfaces 116-118 of recesses 113 and 114. Annular wall 71 is formed with upper and lower shoulders 157 and 158 similar to upper and lower shoulders 121 and 122. The shoulders 157 and 158 have respective upper and lower limiting surfaces 161 and 162 similar to upper and lower limiting surfaces 123 and 124. A slot 163 is provided for each recess in the annular wall 171 and commences where base 151 intersects outer surface 76 for serving, like slots 111 and 112, as an entrance to the recess.

One embodiment of a bone plate suitable for use with bushing 146 is illustrated in FIGS. 21-24. Bone plate 171 therein is substantially similar to bone plate 32 and like reference numerals have been used to describe like elements of bone plates 171 and 32. Head and neck 41 and 42 of bone plate 171 are provided with a plurality of apertures 172 that can be of any suitable type and in one embodiment similar to aperture 102 of bone plate 32. Like reference numerals have been used to described like features of apertures 172 and 102. Each of the apertures 172 is provided with first and second transversely-aligned pins 176 and 177 which extend inwardly into the aperture in opposite-facing diametric alignment. First and second pins 176 and 177 can be of any suitable type, for example any of the types discussed above, and in one embodiment are substantially similar to first and second wings 81 and 82 of bushing 33. The first and second wings 176 and 177 each include a center 86 and front and rear winged portions 87 and 88. A top ramped surface 91 and a bottom ramped surface 92 are also provided on each of the winged portions 87 and 88 of the pins 176 and 177.

Each of the bushings 146 is placed within its respective aperture 172 in a manner similar to which bushings 33 are placed in apertures 102 of bone plate 32. In one such placement method, each bushing 146 is aligned vertically relative to outer surface 48 of the bone plate 171, that is the plane of the bushing extends perpendicular to the plane of the bone plate, and slots 163 on opposite sides of the bushings aligned with the forward winged portion 87 of respective first and second wings 176 and 177 provided in the bone plate. The bushing 146 is moved forwardly into the bone plate, guided by wings 176 and 177 traveling through slots 163 into respective first and second recesses 147 and 148, until the forward winged portion 87 of the wings 176 and 177 engages bottom surface 152 of the recesses 147 and 148. Thereafter, bushing 146 is rotated, guided by the travel of the forward winged portion 87 of first and second wings 176 and 177 on lower ramped surface 153 of the recesses, until the bushing is disposed in a horizontal position such that the plane of the bushing is in the plane of the bone plate.

Any suitable type of bone screw, solid or cannulated, may.be used with bone fastening assembly 31. One suitable type of bone screw 34 is illustrated in FIGS. 25-27 and is made from any suitable material such as a composite material or metal and is preferably made from stainless steel or titanium. The screw 34 includes an elongate shaft 186 extending along a longitudinal axis 187 and having a proximal portion or shaft segment 191, a distal portion or shaft segment 192 and a central portion or shaft segment 193 intermediate the proximal and distal portions 191 and 192. The shaft 186 is provided with external threads 196 formed by a raised helical ridge 197 having an outer diameter 198 which defines the outer diameter of shaft 186. Intermediate adjacent portions of the helical ridge 197 is a helical base 201 having an inner diameter 202 defining the inner diameter of the shaft. Shaft 186 is further provided with a pointed distal tip 203 that is self tapping and optionally self drilling. A head 204 is joined to the proximal portion 191 of the shaft 186 by a neck 205. The head 204 is preferably tapered as it extends distally so as to be conically shaped and is preferably externally threaded. Neck 205 is preferably tapered.

The proximal and distal portions 191 and 192 of the shaft 186, shown most clearly in FIG. 26 where the external treads of screw 34 have been removed from the shaft 186 and head 204 for simplicity, can be of any suitable length relative to the length of central portion 193. Preferably, proximal and distal portions 191 and 192 are of approximate equal length and are sized relative to central portion 193 so as to approximate the thickness of the outer rigid portions of the bone of a mammalian body. Central portion 193 preferably approximates the central, non-ridged portion of a mammalian bone. More specifically, each of proximal portion 191 and distal portion 192 of the screw 34 can have a length ranging from three to ten millimeters and preferably approximately five millimeters. The central portion 193 of the screw varies in length depending on the type and thus length of the screw. Screw 34 can have a length ranging from 10 to 150 millimeters.

The outer and inner diameters 198 and 202 of shaft 196 are configured to increase the force necessary to pull screw 34 out from a bone in which it is being used to secure a bone plate. It is preferable that such pullout force be high so as to inhibit undesirably dislodging of a bone screw and plate from a bone. In this regard, helical ridge 197 preferably has a constant outer diameter 198 over the length of shaft 186. The outer diameter can range from two to ten millimeters. In addition, inner diameter 202 of helical base 201 is preferably constant over the length of central portion 193 of the shaft. Proximal and distal portions 191 and 192 of the shaft preferably have an inner diameter 202 which decreases in a distal direction so that each of the proximal and distal portions 191 and 192 tapers distally. The amount of taper in proximal and distal portions 191 and 192 can vary, and preferably ranges from 0.01 to 0.30 millimeters and more preferably approximately 0.1 millimeters over the length of each such portion 191 and 192.

Head 204 is preferably formed with at least one drive socket and, as illustrated in FIGS. 25 and 27, preferably a first or inner drive socket 206 and a second or outer drive socket 207 for use with respective first and second drive elements (not shown). Each of the drive sockets 206 and 207 is centered on longitudinal axis 187. Inner or primary drive socket 206 can be of any suitable type and is shown in FIG. 27 as having an hexagonal or hex-head configuration formed from six operable surfaces 208 extending parallel to axis 187. Other suitable configurations for inner drive socket include a square-shaped configuration (not shown) and a star-shaped configuration (not shown), among others. The primary drive socket 206 has a maximum transverse dimension or diameter 209, defined as the greatest diametric distance traversed by the operable surfaces 208 of the inner drive socket 206, which is shown in FIG. 27 as being the distance between one point of intersection of two operable surfaces 208 of the hexagonal configuration and the opposing point of intersection of two other operable surfaces 208 of such configuration. Outer or secondary drive socket 207 can also be of any suitable configuration such as a cross-shaped configuration having a plurality of four radially-extending slits 211 defined by operable surfaces 212 extending perpendicular to longitudinal axis 187. The slits 211 are preferably distinct from operable surfaces 208 and have a maximum transverse dimension or diameter 213, defined in the same manner as maximum diameter 211, that is greater than the maximum diameter 211 of inner drive socket 206. Maximum diameter 213 is the distance between the ends of two opposing slits 211 forming the cross configuration of the secondary drive socket.

The operation and use of the bone fastening assembly 31 of the present invention is described with respect to bone plate 32 having bushings 33 therein and having a plurality of apertures 102 and 103 and treaded holes 57 formed therein. The bushing 33 is inserted into the bone plate bone plate 32 in the manner described above either before delivery of the bone fastening assembly to the site of operation or immediately prior to such procedure. Head 41 of the bone plate 32 can be attached to a targeting guide (not shown) which allows for insertion of the entire shaft 43 of the plate bone plate 32 in a percutaneously manner and allows a bone drill (not shown) and bone screws 34 to be directed in an optimal direction to engage the bone plate via a percutaneous technique. Relative to the bone being treated, neck 42 of the plate 32 is located at the metaphyseal region of the bone. When a screw 34 is placed in the center of threaded bore 57 having an oval ramped surface 61, for example by a targeting device or guide, the plate moves relative to the bone as the locking screw 34 travels down the smooth oval-shaped ramped surface 61 of the threaded hole 57. The neck 205 of a screw 34 engages the plate 32 when the hole in the bone is drilled eccentrically within the plate and moves the plate relative to the bone and vice versa. Screws with a threaded head or a non-threaded head can be placed into the bone plate 32 to allow for compression across the fracture site if needed. At least one threaded bore 74 of a bushing 33 located in neck 42 of the bone plate 32 is directed toward the area at the end of the bone at an angle allowing for buttressing the side of the bone opposite to the plate 32.

In one suitable procedure, before complete insertion of a bone screw 34 into a bushing 33 disposed in aperture 103 formed with a circumferential groove 131 therein, for example apertures 103 located in neck 42 of bone plate 32, the bushing is rotated within the aperture 103 until pivot axis 127 of the bushing 33 is in a desired location in the plane of the bone plate. Such rotation is guided by the travel of the first and second wings 81 and 82 in circumferentially-extending groove 131. Once in such position, upper and lower planar surfaces 132 and 133 within the bone plate limit the pivotably movement of the bushing 33 within the bone plate. In this manner, the bushing can rotate 360 degrees within the bone plate 32 to allow for the screw to be inserted into the bone in any desired direction.

When a bone screw 34 is threaded into bushing 33, the travel of the screw 34 through the tapered threaded bore 74 of the bushing causes the annular wall 71 of the bushing to radially expand so that outer surface 76 of the bushing is fully engaged and in compression by internal surface 106 of the bone plate. The slit 77 in the bushing 33 permits such radial expansion of the bushing. The complete recessing of bushing 33 within the aperture 103, specifically the complete concentric engagement of outer bushing surface 76 by internal surface 106 of the bone plate, enhances the rigid fixation of the bushing within the bone plate. In this manner, bushing 33 is affixed rigidly into aperture 103 of the bone plate 32 by the fastening of bone screw 34 into the bone plate 32 and the underlying bone of the mammalian body being treated. The increased friction between bushing outer surface 76 and bone plate internal surface 106 further increases the resistance to motion of the screw-bushing-plate assembly in all directions when the screw 34 is fully seated in the plate and underlying bone.

The tapered inner diameter 202 at the proximal and distal portions 191 and 192 of bone screw 34 enhances the frictional engagement of a screw when fully seated within bone plate 32 and the bone being treated. Specifically, such taper results in increased radial force exerted by the near and far outer wall of the bone on the screw as the screw reaches its fully seated position within the bone. The constant outer diameter 198 of threads 196 reduces undesirable pullout of the screw from the bone should the screw be backed out of the bone plate 32 and the bone being treated for some reason during the procedure before being reseated within the bone at a later point in the procedure.

Primary drive socket 206 can be utilized with the primary drive element for moving bone screw 34 longitudinally relative to bone plate 32, for example either advancing or retracting the screw relative to the bone plate, throughout the procedure. Should the primary drive socket become stripped or otherwise inoperable during the procedure, a secondary drive element can be used with the secondary drive socket 207 for further advancing or retracting the bone screw 34 relative to the bone plate 32 and the bone being treated. The slits 211 forming secondary drive socket 207 extend radially beyond the operable surfaces 208 of primary drive socket 206 and are thus not stripped or otherwise rendered inoperable when utilizing the primary drive socket 206. It is appreciated that the secondary drive socket 207 can be of any suitable configuration in which the operable surfaces 212 thereof are unaffected by any stripping or otherwise rendering inoperable of the surfaces 208 of the primary drive socket 206.

It can be seen from the foregoing that a new bone fastening assembly has been provided. The bone plate of the assembly allows for controlled directional insertion of bone screws into a bone being treated. The screws can be pivoted relative to the bone plate, and such pivoting can desirably be limited to movement within a plane. The plane of such movement can be adjusted relative to the bone plate. Bone screws having an increased pullout force are provided. The head of the screws can include a secondary drive socket that is not harmed by any stripping or other ruining of the primary drive socket so as to permit further advancement or retraction of the screws should the primary drive socket become inoperable.

What is claimed is:

1. A bone attachment screw for use with a bone plate in a bone having an outer wall comprising an elongate shaft having a proximal portion and a distal portion and a central portion intermediate the proximal and distal portions, the shaft having external threads formed by a raised helical ridge with an outer diameter and a recessed helical base with an inner diameter extending between adjacent portions of the helical ridge, a head joined to the proximal portion of the shaft, the outer diameter of the helical ridge being substantially constant along the shaft and the inner diameter of the base at the proximal portion and the distal portion tapering inwardly as such portions extend away from the head and the inner diameter of the base at the central portion being substantially constant whereby the tapered inner diameter at each of the proximal and distal portions of the shaft is adapted to extend into the outer wall of the bone when securing the bone plate to the bone and serves to enhance the pullout force of the screw in the outer wall of the bone.

2. A screw as in claim 1 wherein the head is provided with an inner drive socket and an outer drive socket.

3. A bone attachment screw for use with a bone plate and first and second drive elements comprising a head and a threaded shaft joined to the head, the head and the shaft extending along a longitudinal axis, the head being provided with a first inner drive socket and a second inner drive socket, the first inner drive socket being centered on the longitudinal axis and being formed by a plurality of first operable surfaces having a first maximum diameter relative to the longitudinal axis, the second inner drive socket being centered on the longitudinal axis and being formed by a plurality of second operable surfaces having a second maximum diameter relative to the longitudinal axis, the second maximum diameter being greater than the first maximum diameter whereby if the first inner drive socket becomes stripped by the first drive element while longitudinally moving the bone attachment screw relative to the bone plate then the second inner drive socket can be utilized by the second drive element for further longitudinally moving the bone attachment screw relative to the bone plate.

4. A screw as in claim 3 wherein the first inner drive socket is hexagonal in shape.

5. A screw as in claim 3 wherein the first inner drive socket is square in shape.

6. A screw as in claim 3 wherein the first inner drive socket is generally star shaped.

7. A screw as in claim 3 wherein the second inner drive socket is cross shaped.

* * * * *